(12) United States Patent
Yamana et al.

(10) Patent No.: US 11,819,851 B2
(45) Date of Patent: Nov. 21, 2023

(54) MICROFLUIDIC DEVICE WITH VENTED MICROCHAMBERS

(71) Applicant: QIAGEN SCIENCES, LLC, Venlo (NL)

(72) Inventors: Kabir James Yamana, Cambridge, MA (US); Sean Yamana-Hayes, Cambridge, MA (US)

(73) Assignee: QIAGEN SCIENCES, LLC, Venlo (NL)

( * ) Notice: Subject to any disclaimer, the term of this patent is extended or adjusted under 35 U.S.C. 154(b) by 176 days.

(21) Appl. No.: 17/377,021

(22) Filed: Jul. 15, 2021

(65) Prior Publication Data

US 2021/0379593 A1 Dec. 9, 2021

Related U.S. Application Data

(62) Division of application No. 15/873,722, filed on Jan. 17, 2018, now Pat. No. 11,154,864.

(51) Int. Cl.
| | |
|---|---|
| *B81B 1/00* | (2006.01) |
| *B01L 3/00* | (2006.01) |
| *C12Q 1/686* | (2018.01) |

(52) U.S. Cl.
CPC ... *B01L 3/502784* (2013.01); *B01L 3/502723* (2013.01); *B01L 3/502738* (2013.01); *C12Q 1/686* (2013.01); *B01L 2200/0684* (2013.01); *B01L 2200/10* (2013.01); *B01L 2300/087* (2013.01); *B01L 2300/0819* (2013.01); *B01L 2300/0829* (2013.01); *B01L 2300/165* (2013.01); *B01L 2400/0688* (2013.01)

(58) Field of Classification Search
None
See application file for complete search history.

(56) References Cited

U.S. PATENT DOCUMENTS

| | | |
|---|---|---|
| 4,632,244 A | 12/1986 | Landau |
| 5,229,297 A | 7/1993 | Schnipelsky et al. |
| (Continued) | | |

FOREIGN PATENT DOCUMENTS

| | | |
|---|---|---|
| EP | 0488769 A2 | 6/1992 |
| EP | 1065378 A2 | 1/2001 |
| (Continued) | | |

*Primary Examiner* — Paul S Hyun
(74) *Attorney, Agent, or Firm* — MCBEE MOORE & VANIK IP, LLC

(57) ABSTRACT

A microfluidic device with a microfluidic circuit including an array of fluidly coupled microchambers. Each microchamber includes a reaction chamber and an associated vent chamber. The microfluidic circuit may be arranged so that a fluid sample introduced to microfluidic device flows into the reaction chamber and air or other gas present in the reaction chamber is vented from the microchamber through the vent chamber. The microchamber may be configured to allow only the flow of air into the vent chamber from the reaction chamber until the air has been displaced from the reaction chamber by the fluid sample and/or a predefined volume of the fluid sample has been received in the reaction chamber. The microchamber may be further configured to release the fluid sample to thereafter flow from the reaction chamber into the vent chamber.

11 Claims, 10 Drawing Sheets

(56) References Cited

U.S. PATENT DOCUMENTS

| | | | |
|---|---|---|---|
| 5,508,197 A | 4/1996 | Hansen et al. | |
| 6,251,343 B1 | 6/2001 | Dubrow et al. | |
| 6,268,131 B1 | 7/2001 | Kang et al. | |
| 6,408,878 B2 | 6/2002 | Unger et al. | |
| 6,503,757 B1 | 1/2003 | Chow | |
| 6,645,432 B1 | 11/2003 | Anderson et al. | |
| 6,719,868 B1 | 4/2004 | Schueller et al. | |
| 6,793,753 B2 | 9/2004 | Unger et al. | |
| 6,929,030 B2 | 8/2005 | Unger et al. | |
| 7,195,670 B2 | 3/2007 | Hansen et al. | |
| 7,216,671 B2 | 5/2007 | Unger et al. | |
| 7,307,802 B2 | 12/2007 | Unger | |
| 7,316,802 B2 | 1/2008 | Blankenstein et al. | |
| 7,318,912 B2 | 1/2008 | Pezzuto et al. | |
| 7,323,143 B2 | 1/2008 | Anderson et al. | |
| 7,476,363 B2 | 1/2009 | Unger et al. | |
| 7,479,186 B2 | 1/2009 | Quake et al. | |
| 7,494,555 B2 | 2/2009 | Unger et al. | |
| 7,588,672 B2 | 9/2009 | Unger et al. | |
| 7,601,270 B1 | 10/2009 | Unger et al. | |
| 7,604,965 B2 | 10/2009 | Mcbride et al. | |
| 7,666,361 B2 | 2/2010 | Mcbride et al. | |
| 7,691,333 B2 | 4/2010 | Mcbride et al. | |
| 7,704,735 B2 | 4/2010 | Facer et al. | |
| 7,749,737 B2 | 7/2010 | Mcbride et al. | |
| 7,766,055 B2 | 8/2010 | Unger et al. | |
| 7,815,868 B1 | 10/2010 | Jones et al. | |
| 7,837,946 B2 | 11/2010 | Mcbride et al. | |
| 7,867,454 B2 | 1/2011 | Goodsaid et al. | |
| 7,867,763 B2 | 1/2011 | Facer et al. | |
| 7,906,072 B2 | 3/2011 | Unger et al. | |
| 8,048,378 B2 | 11/2011 | Unger et al. | |
| 9,039,993 B2 | 5/2015 | Yamana et al. | |
| 9,163,277 B2 | 10/2015 | Yamana et al. | |
| 11,154,864 B2 * | 10/2021 | Yamana | B01L 3/502738 |
| 2002/0047003 A1 | 4/2002 | Bedingham et al. | |
| 2004/0096358 A1 | 5/2004 | Blankenstein et al. | |
| 2004/0171170 A1 | 9/2004 | Sandell | |
| 2007/0014695 A1 | 1/2007 | Yue et al. | |
| 2011/0005378 A1 | 3/2011 | Bedingham et al. | |

FOREIGN PATENT DOCUMENTS

| | | |
|---|---|---|
| EP | 1195523 A2 | 4/2002 |
| JP | 2004-170408 A | 6/2004 |
| JP | 2006-197906 A | 8/2006 |
| JP | 2009-109222 A | 5/2009 |
| WO | 9013016 A1 | 11/1990 |
| WO | 01/01025 A2 | 1/2001 |
| WO | 02/43615 A2 | 6/2002 |
| WO | 2006116616 A2 | 11/2006 |
| WO | 2013175833 A1 | 1/2016 |

* cited by examiner

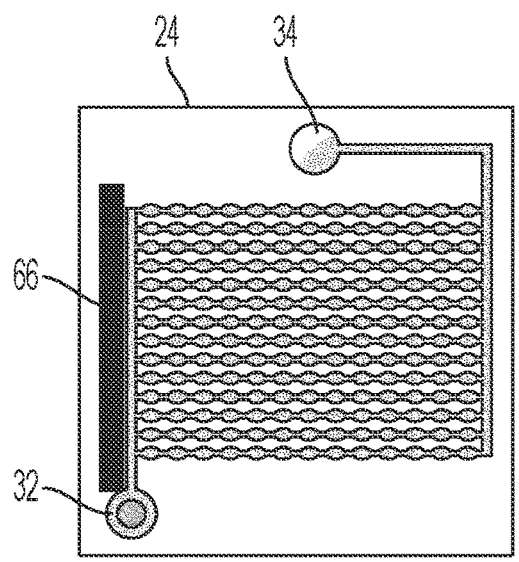 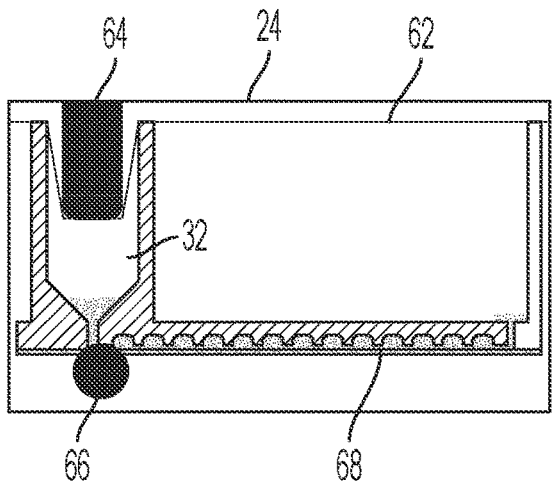
FIG. 17A    FIG. 17B
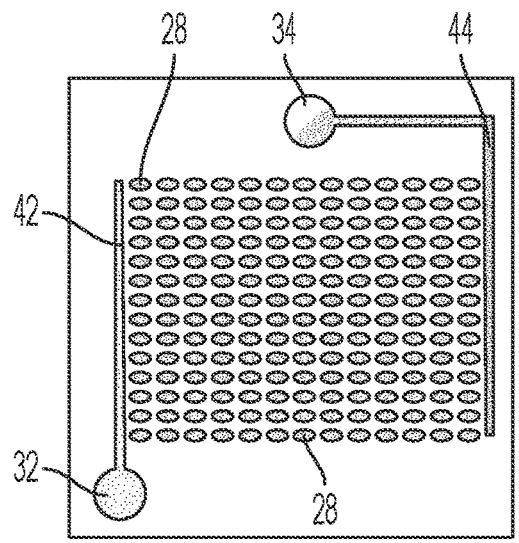 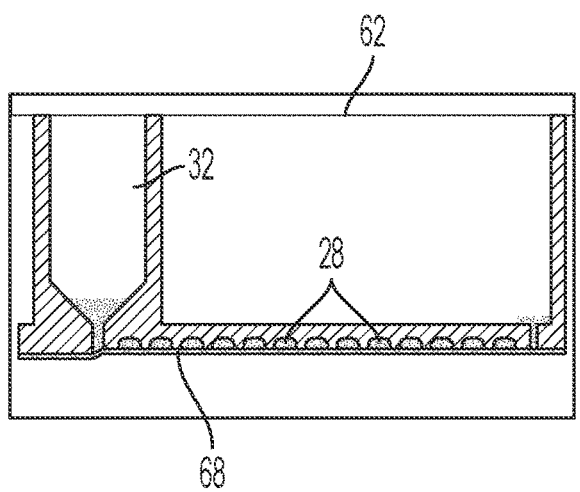
FIG. 18A    FIG. 18B

MICROFLUIDIC DEVICE WITH VENTED MICROCHAMBERS

CROSS-REFERENCE TO RELATED APPLICATIONS

This application is a Divisional of U.S. patent application Ser. No. 15/873,722, filed Jan. 17, 2018 and is herein incorporated in its entirety.

FIELD

Aspects of the present disclosure relate generally to methods and devices for microfluidic handling.

DISCUSSION OF RELATED ART

Polymerase chain reaction (PCR) is a technique used in molecular biology to amplify a single copy or a few copies of a segment of DNA across several orders of magnitude, generating millions to billions of copies of a particular DNA sequence. It is an easy, inexpensive, and reliable way to repeatedly replicate a focused segment of DNA, a concept which is applicable to numerous fields in modern biology and related sciences.

PCR is a common technique used in clinical and research laboratories for a broad variety of applications. Examples of such applications include DNA cloning for sequencing, gene cloning and manipulation, gene mutagenesis; construction of DNA-based phylogenies, or functional analysis of genes; diagnosis and monitoring of hereditary diseases; amplification of ancient DNA; analysis of genetic fingerprints for DNA profiling (for example, in forensic science and parentage testing); and detection of pathogens in nucleic acid tests for the diagnosis of infectious diseases.

PCR methods typically rely on thermal cycling, which involves exposing reactants to cycles of repeated heating and cooling, permitting different temperature-dependent reactions, specifically DNA melting and enzyme-driven DNA replication, to quickly proceed many times in sequence. Primers (short DNA fragments) containing sequences complementary to the target region, along with a DNA polymerase, enable selective and repeated amplification. As PCR progresses, the DNA generated is itself used as a template for replication, setting in motion a chain reaction in which the original DNA template is exponentially amplified.

For example, when exposed to a relatively high temperature (e.g., greater than 90 C), double helix molecules of a DNA sample are separated into single strands. At a relatively lower temperature (e.g., 50-70 C), DNA primers attach at target sites to single strands of the DNA sample. At an intermediate range of temperature (e.g., 60-80 C), the polymerase facilitates elongation of DNA fragments formed from the initial attachment of primers to the single-stranded DNA molecules. The double-stranded DNA products of one PCR cycle can then be split at the relatively high temperature range and bound to new primer strands, doubling the amount of DNA in every cycle until the reagents are exhausted. Thus, the concentration of a DNA sample containing a target DNA sequence, when subject to PCR, may increase exponentially.

Digital PCR (dPCR) is a type of PCR analysis that involves dividing a DNA sample into a large number of separate aliquots, and amplifying the aliquots to determine whether a molecule of target DNA was present within the aliquot. Based on the number of aliquots that have undergone exponential growth, the original concentration of DNA prior to partitioning may be determined.

Digital PCR can provide increased detection specificity. In cases where the target is relatively rare compared to the amount of non-target DNA, the background DNA can compete for reagents and cause non-specific amplification. Partitioning the sample into many small chambers on a dPCR microplate increases the effective concentration of rare targets in the partitions.

It is an object of the invention to provide a microfluidic device for handling fluid samples which may undergo dPCR or other techniques associated with molecular biology.

SUMMARY

The present disclosure relates to a microfluidic device, such as a microplate, for handling fluid samples which may be subjected to various techniques associated with molecular biology applications.

According to one aspect, the microfluidic device comprises at least one microfluidic well configured to receive a fluid sample. The at least one microfluidic well includes a plurality of microchambers and at least one microfluidic channel fluidly coupling the plurality of microchambers. Each microchamber includes a reaction chamber and a vent chamber, the reaction chamber configured to receive the fluid sample from the microfluidic channel and the vent chamber configured to vent gas from the reaction chamber via the microfluidic channel as the fluid sample flows into the reaction chamber.

According to another aspect, the microfluidic device comprises at least one microfluidic well configured to receive a fluid sample, and a microfluidic circuit provided in the at least one microfluidic well. The microfluidic circuit is configured to distribute the fluid sample within the microfluidic well. The microfluidic circuit includes a plurality of reaction chambers, at least one microfluidic channel fluidly coupling the reaction chambers, and a plurality of microfluidic valves associated with the plurality of reaction chambers. Each microfluidic valve is fluidly coupled to an associated reaction chamber. Each reaction chamber is configured to receive a fluid sample from the microfluidic channel and each microfluidic valve is configured to vent gas from a corresponding reaction chamber via the microfluidic channel as the fluid sample flows into the reaction chamber.

According to another aspect, a method is provided for handling a fluid sample. The method comprising (a) delivering a fluid sample to a microfluidic device including a plurality of microchambers and at least one microfluidic channel fluidly coupling the plurality of microchambers. Each microchamber includes a reaction chamber and a vent chamber fluidly coupled to the reaction chamber. The method further comprising (b) directing the fluid sample into the reaction chamber of each microchamber, and (c) venting gas from the reaction chamber via the vent chamber as the fluid sample flows into the reaction chamber.

The foregoing is a non-limiting summary of the disclosure. Other aspects, embodiments and/or features will become apparent from the following description.

Various embodiments of the present disclosure may provide certain advantages and may overcome certain drawbacks of prior microfluidic devices. Embodiments of the disclosure may not share the same advantages, and those that do may not share them under all circumstances.

BRIEF DESCRIPTION OF DRAWINGS

Aspects of the present disclosure are described below, by way of example, with reference to the accompanying drawings in which like numerals reference like elements, and wherein:

FIG. 16A depicts the microfluidic system filled with a fluid sample (shading). FIG. 16B (side view) depicts the fluid sample may be injected into the microfluidic circuit using a piston 64 or other suitable device which presses the plate seal 62 into the circuit inlet 32 to create a pressure differential between the circuit inlet and circuit vent causing the fluid to flow through the microfluidic circuit comprising microchambers 28. In addition to air, excess fluid within the microfluidic circuit may exit through the circuit vent. A bottom seal 68 of the microplate blocks off the microfluidic 30 channels and isolated the fluid samples held by each of the microchambers 28.

FIG. 17A-B depicts a schematic illustration of a well 24 with a circuit inlet 32 is coupled to the inlet channel 42 in fluid communication with a plurality of microchambers coupled to an outlet channel coupled to a circuit vent 34. With the microfluidic circuit filled with the fluid sample (shading), a roller 66 may be used to compress the microplate [top view (A)]. A well 24 comprises a plurality of microchambers coupled to a circuit inlet 32 configured to receive a fluid sample that is to be distributed throughout the microfluidic circuit coupled to an outlet channel. A bottom seal 68 of the microplate blocks off the microfluidic channels and isolated the fluid samples held by each of the microchambers. A fluid sample may be injected into the microfluidic circuit using a piston 64 or other suitable device which presses the plate seal 62 into the circuit inlet 32 to create a pressure differential between the circuit inlet and circuit vent causing the fluid to flow through the microfluidic circuit. When the microfluidic circuit filled with the fluid sample (shading), a roller 66 may be used to compress a bottom seal 68 of the microplate [side view (B)].

FIG. 18A-B bottom seal of the microplate may be compressed to block off the microfluidic channels and isolate the fluid samples held by each of the microchambers 28. This isolates the circuit inlet 32 and inlet channel from the microchambers 28 and the outlet channel 44 coupled to a circuit vent 34 from the microchambers 28 [top view (A)]. FIG. 18B depicts how the microchambers 28 are blocked off to isolate the fluid samples held by each of the microchambers 28 with the bottom seal 68 below and the plate seal 62 above and the circuit inlet 32 [side view].

FIG. 19A-B depicts a schematic illustration of a well 24 with a plurality of microchambers 28 and a circuit vent 34 [top view (A)]. A well 24 comprises a plurality of microchambers 28 and a circuit inlet 32 configured to receive a fluid sample with a bottom seal 68 of the microplate and a plate seal 62 [side view (B)]. Microchambers 28a containing the target DNA 10 become fluorescent. The microplate may then be imaged by the instrument to count the number of positive microchambers 28a.

DETAILED DESCRIPTION OF INVENTION

Figure 1:
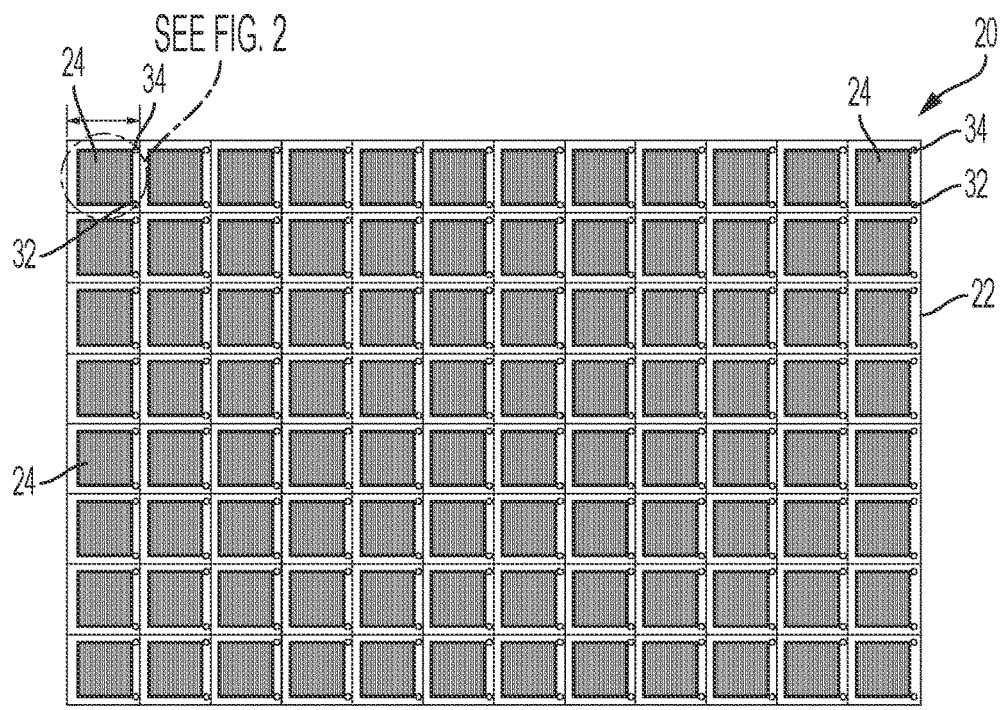
FIG. 1 is top view of a microfluidic device according to one embodiment.

It should be understood that aspects of the present disclosure are described herein with reference to the figures, which show illustrative embodiments in accordance with aspects of the disclosure. The illustrative embodiments described herein are not necessarily intended to show all aspects of the disclosure, but rather are used to describe a few illustrative embodiments. Thus, aspects of the disclosure are not intended to be construed narrowly in view of the illustrative embodiments. It should be appreciated, then, that the various concepts and embodiments discussed herein may be implemented in any of numerous ways, as the disclosed concepts and embodiments are not limited to any particular manner of implementation. In addition, it should be understood that aspects of the disclosure may be used alone or in any suitable combination with other aspects of the disclosure.

The present disclosure relates to a microfluidic device for handling samples of fluid material that are to be subjected to techniques associated with molecular biology, and is particularly suitable for use with digital PCR (dPCR) techniques. For ease of understanding, and without limiting the scope of the disclosure, the microfluidic device is described below particularly in connection with dPCR techniques including, but not limited to, DNA melting and enzyme-driven DNA replication. It should be understood, however, that the microfluidic device is not so limited and may be employed with other clinical and/or research techniques associated with molecular biology, as should be apparent to one of skill in the art. For example, and without limitation, the microfluidic device may be employed for DNA cloning for sequencing, gene cloning and manipulation, gene mutagenesis; construction of DNA-based phylogenies, or functional analysis of genes; diagnosis and monitoring of hereditary diseases; amplification of ancient DNA; analysis of genetic fingerprints for DNA profiling; and detection of pathogens in nucleic acid tests for the diagnosis of infectious diseases. The microfluidic device may include one or more features, each independently or in combination, contributing to such attributes.

The present disclosure is more particularly directed to a microfluidic device including one or more microfluidic wells for receiving one or more fluid samples that are to be analyzed using a dPCR technique, although the disclosure is not so limited. Each microfluidic well may include a plurality of microchambers configured to receive a volume of the fluid sample delivered to the well. Each microchamber may be fluidly coupled to an adjacent microchamber by a microfluidic channel or a segment of the channel. The microchambers may be fluidly coupled by one or more microfluidic channels extending across the well. For example, the microchambers may be arranged in separate groups of microchambers with each group of microchambers being fluidly coupled by a separate microfluidic channel extending across the well. Such an arrangement creates a microfluidic circuit whereby a fluid sample may flow from one microchamber to an adjacent microchamber via the microfluidic channels.

Prior to receiving a fluid sample in the microfluidic well, the microchambers and microfluidic channels of the well are typically filled with a gas, such as air. For convenience, the disclosure will hereafter refer to air, although other gases suitable for a dPCR technique may be present in the microfluidic circuit. Introducing a fluid sample into the microfluidic well requires displacing the air from the microchambers and microfluidic channels to permit the fluid sample to flow along and fill the microfluidic circuit. Any air remaining in the microfluidic circuit could potentially form bubbles in the microchambers which may impact the accuracy of the dPCR technique.

Bubble formation in a microfluidic device may be addressed by varying the aspect ratio of the depth-to-diameter of the microchamber. For example, a microchamber configured with a relatively shallow depth and large diameter (i.e., relatively small aspect ratio) may be effective at avoiding the formation and/or entrapment of air bubbles as fluid flows into the microchamber. The inventors have appreciated that such a microchamber configuration can limit the number of microchambers within a microfluidic well. The inventors have further appreciated that it may be desirable for some applications of a microfluidic device to increase the number of microchambers within a microfluidic well. Increasing the number of the microchambers would require the use microchambers having a relatively larger aspect ratio (i.e., smaller diameter, larger depth) to achieve the same volume as a microchamber having a smaller aspect ratio. However, the inventors have appreciated that microchambers configured with a relatively higher aspect ratio may be more susceptible to bubble formation. For example, it may be desirable to fluidly couple microchambers with relatively shallow microfluidic channels whereby the microchambers are substantially deeper than the microfluidic channels. As the fluid sample flows into the microchamber through an inlet channel, gas within the microchamber is displaced by the entering fluid and escapes through an outlet channel. However, it may be possible for the fluid sample to reach the outlet channel before completely filling the microchamber. Once the fluid sample reaches and enters the outlet channel, no additional gas can escape from the microchamber which may result in a bubble becoming trapped within the microchamber.

The inventors have appreciated that a microfluidic device that reduces, if not eliminates, the presence of bubbles in the microfluidic circuit, particularly the microchambers within the microfluidic well, would be advantageous, particularly for dPCR techniques. The inventors have further appreciated that it would be beneficial to develop a microfluidic device that reduces the potential of bubble formation in the microchambers in a cost effective manner.

A microfluidic device of the present disclosure may be provided with an array of microchambers in which each microchamber includes a reaction chamber and an associated vent chamber. The microfluidic circuit may be arranged so that a fluid sample introduced to the microfluidic well flows into the reaction chamber and air or other gas present in the reaction chamber is vented from the microchamber through the vent chamber. The microchamber may be configured to allow only the flow of air into the vent chamber from the reaction chamber until such time that the air has been displaced from the reaction chamber by the fluid sample and/or a predefined volume of the fluid sample has been received in the reaction chamber. The microchamber may be further configured to allow the fluid sample to thereafter flow from the reaction chamber into the vent chamber. The array of microchambers may be arranged so that fluid exiting the vent chamber may flow to the reaction chamber of the next microchamber in the microfluidic circuit through a microfluidic channel fluidly coupling the microchambers. The microfluidic channel may be shallower than the microchambers to facilitate sealing of the channels after the microchambers are filled with the fluid sample.

The microchamber may include a microfluidic valve or valve-like arrangement between the reaction chamber and the vent chamber to control the flow the fluid and air. In one aspect, the microchamber may be configured such that the vent chamber is smaller than the reaction chamber in at least one dimension and configured to create sufficient surface tension at the transition from the reaction chamber to the vent chamber to hold back the fluid from entering the vent chamber until the surface tension is overcome by the pressure of the fluid. In this manner, a microfluidic valve is formed at the transition or entrance to the vent chamber which acts in a passive manner with no active actuation of the valve necessary to permit fluid flow.

The vent chamber may be configured to have a depth which is the same or even deeper than the reaction chamber. The vent chamber may be connected to the reaction chamber along a majority, if not the entirety, of the depth of the microchamber so that, as the fluid sample flows into the microchamber, gas can escape until the fluid fills the full depth of the reaction chamber. Alternatively, for some applications where it may be desirable to entrap a predefined bubble, the depth of the vent chamber may be less than the depth of, and extend along only a portion of, the reaction chamber. When the fluid sample reaches the portion of the reaction chamber not coupled to the vent chamber, the volume of gas remaining in the reaction chamber cannot be vented and becomes entrapped thereby forming a bubble defined by the portion of the reaction chamber not vented by the vent chamber.

Each microfluidic well may be provided with a main inlet for receiving a fluid sample and a main vent for venting air and any excess fluid from the microchambers as the fluid sample is delivered to the well. The main inlets to the microfluidic wells may be arranged to accommodate pipetting or other techniques for delivering fluid samples to each microfluidic well, as should be apparent to one of skill in the art.

Each microfluidic well may be configured to distribute portions of the fluid sample to each of the microchambers. For example, and without limitation, the microchambers may be arranged in multiple groups with a portion of the fluid sample being delivered to each group of microchambers by a separate microfluidic channel fluidly coupling each microchamber of the group. For some applications, the microchambers of each group may be fluidly coupled in series by a plurality of microfluidic channels or segments of a microfluidic channel. Each group may also be arranged to receive portions of the fluid sample in parallel with each other. However, the present disclosure is not so limited and the microchambers may be arranged and/or fluidly coupled in any suitable manner as should be apparent to one of skill in the art.

In one embodiment shown in FIG. 1, a microfluidic device 20 may include a microplate 22 provided with one or more microfluidic wells 24 for receiving one or more fluid samples that are to be analyzed using, but not limited to, a dPCR technique. Each of the microfluidic wells 24 may receive the same fluid sample or different wells may receive different fluid samples for analysis, as should be appreciated by one of skill in the art.

As illustrated, the microfluidic wells 24 may be arranged in an array having a grid pattern, although other arrangements suitable for a particular technique and/or microfluidic system are contemplated. In one embodiment, the microfluidic device may include ninety-six (96) microfluidic wells arranged in a 8×12 grid pattern. Other arrangements may include, but are not limited to, a microplate with twenty-four (24) microfluidic wells arranged in a grid pattern.

Each microfluidic well 24 may have a microfluidic circuit 26 including a plurality of microchambers 28 fluidly coupled by one or more microfluidic channels 30 extending across the well. The microchambers 28 may be configured to receive and hold a predetermined volume of the fluid sample that is to be subjected to dPCR or other technique. Each microfluidic well 24 may include a primary inlet 32 for receiving the fluid sample that is to be distributed throughout the microfluidic circuit and a primary vent 34 for venting air and excess fluid from the microfluidic circuit.

To facilitate fluid flow through the microfluidic circuit, the microchambers may be arranged in groups or sub-circuits which are fluidly coupled together. In one embodiment illustrated in FIGS. 2-4, the microchambers may be arranged in multiple groups 36 and the microchambers in each group may be fluidly coupled together in series with a microfluidic channel 30 or segments of a microfluidic channel. Each group 36 of microchambers may be arranged to receive fluid flow in parallel with each other. Each group 36 of microchambers may include a microfluidic channel 30 with an inlet end 38 and an outlet end 40. The inlet end 38 may be fluidly coupled to the primary inlet 32 via an inlet microfluidic channel 42 and the outlet end 40 may be fluidly coupled to the primary vent 34 via an outlet microfluidic channel 44. It is to be appreciated that any suitable microfluidic circuit arrangement may be employed to facilitate flow and distribution of the fluid sample as should be apparent to one of skill in the art.

For some applications, it may be desirable to increase the number of microfluidic channels within a microfluidic well. This may be achieved by decreasing the spacing between adjacent microchambers which may involve decreasing the diameter of the microchamber. To maintain the same microchamber volume, the depth of the microchamber would be increased. However, the inventors have appreciated that changing the aspect ratio of the microchamber in this manner may create a less efficient flow of the fluid sample through the microfluidic circuit of the microfluidic well with a higher potential for trapping bubbles in the microchambers.

To address this concern, each microchamber may be configured to vent gas, such as air, as the fluid sample flows into the microchamber in a manner which permits the fluid to efficiently flow through the microfluidic circuit with a reduced incidence of trapping bubbles in the microchamber.

Figure 3:
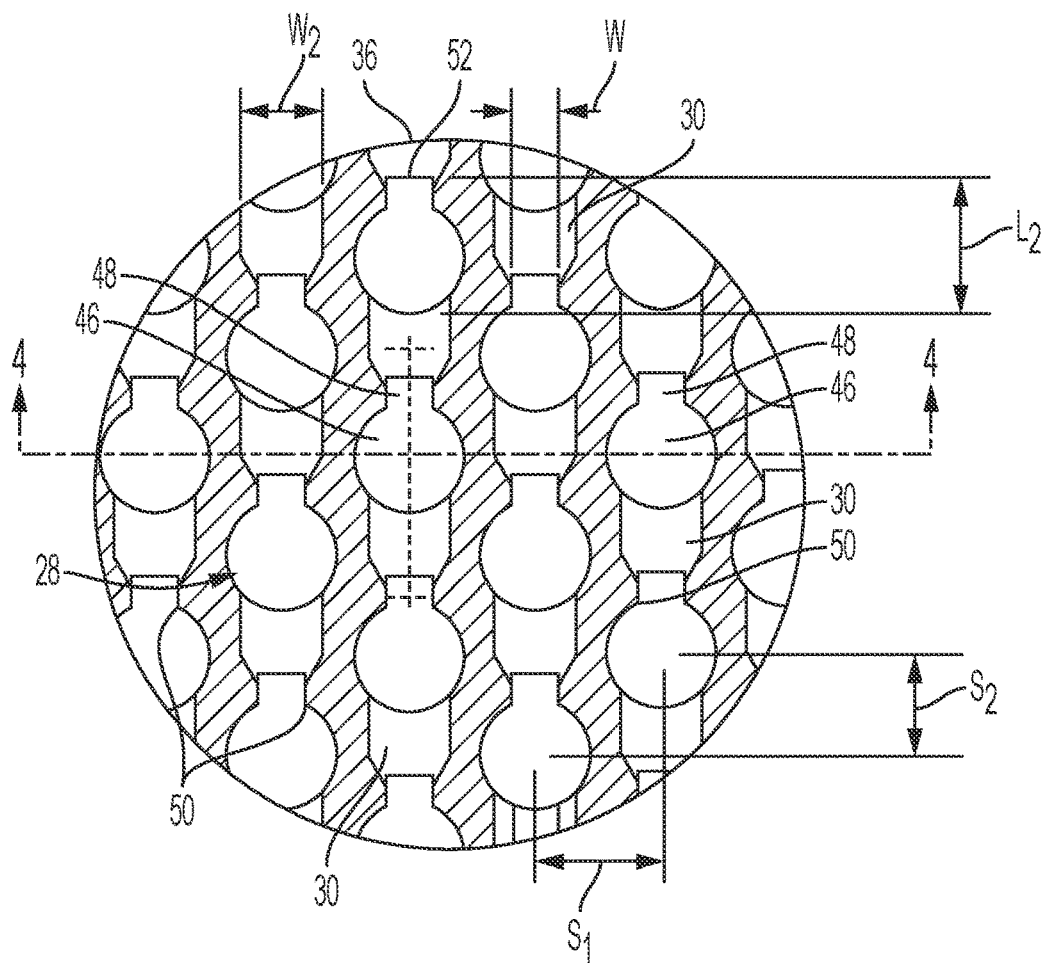
FIG. 3 is an enlarged view of the well of FIG. 2 illustrating microchambers and microfluidic channels of the microfluidic circuit according to one embodiment.
Figure 4:
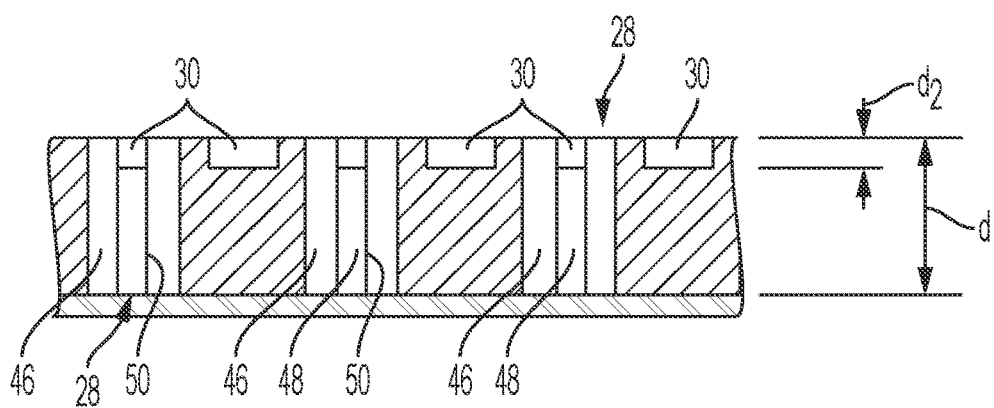
FIG. 4 is a cross-sectional view of the microfluidic circuit taken along section line 4-4 of FIG. 3
Figure 5:
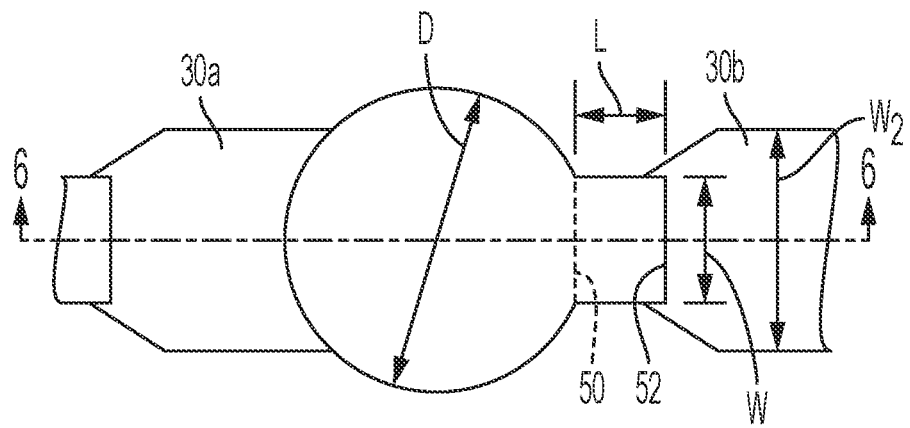
FIG. 5 is an enlarged view of a microchamber according to one embodiment.

In one embodiment illustrated in FIGS. 3-5, each microchamber 28 may include a reaction chamber 46 and an associated vent chamber 48. The reaction chamber 46 is configured to receive and hold a predefined volume of the sample from the microfluidic channel 30 and the vent chamber 48 is configured to vent gas from the reaction chamber 46 as the fluid sample flows into the reaction chamber. When the gas has been vented from at least the reaction chamber and/or the reaction chamber receives a predefined volume of fluid, the fluid sample flows through the vent chamber 48 and continues along the microfluidic channel 30 to the next microchamber in the microfluidic circuit. In this manner, the reaction chamber 46 receives fluid from an upstream segment 30*a* of the microfluidic channel and the fluid passes through the vent chamber to a downstream segment 30*b* of the microfluidic channel. Moreover, air residing in the microfluidic circuit is vented from the microfluidic circuit by the advancing flow of the fluid sample along the microfluidic channel.

As indicated above, the microchamber 28 may include a microfluidic valve or valve-like arrangement to control the flow of fluid and air. In one embodiment, the vent chamber 48 may be configured to act similar to, if not as, a capillary valve or a hydrophobic valve. More particularly, the microchamber 28 may be configured with a narrow hydrophobic stricture 50 to prevent the liquid sample from initially entering the vent chamber 48 until the reaction chamber 46 is essentially free of air that would otherwise form bubbles in the reaction chamber during the filling process. In addition or alternatively, the microchamber 28 may be configured with a narrow hydrophobic stricture 50 to prevent the fluid sample from initially entering the vent chamber 48 until the reaction chamber 46 is filled with a predefined volume of the fluid sample which may be adequate for providing accurate results.

Without wishing to be bound by any particular theory, capillary forces result the interaction of liquid, air and solid surfaces at the interface therebetween. Molecules in the liquid phase are held together by cohesive forces which are balanced in the bulk of the liquid. For liquid molecules at the edge of the liquid, cohesive forces with other liquid molecules are larger than the interaction with adjacent air molecules resulting in the liquid molecules at the interface being pulled together towards the liquid. The overall effect of these forces is to minimize the free surface of the liquid that is exposed to air. The proportionality between the decreased energy of the surface resulting from decreasing the surface area is surface tension.

Surface tension is responsible for an increased pressure required to push liquid into an empty non-wetting passage, such as a capillary. Thus, providing a narrow hydrophobic stricture 50 from the reaction chamber 46 to the vent chamber 48 will prevent the flow of the fluid sample from the reaction chamber to the vent chamber until the surface tension at the stricture is overcome by increased fluid pressure within the reaction chamber. The microchamber may be configured so that the pressure needed to overcome the surface tension occurs when a predefined volume of liquid is present in the reaction chamber which results when air has been displaced from the reaction chamber and into or through the vent chamber.

The capillary effect between the reaction chamber 46 and the vent chamber 48 may be achieved with a microchamber configuration including a narrow stricture 50 located between the chambers. In one embodiment illustrated in FIGS. 3-5, the reaction chamber 46 may have a circular configuration with a diameter D and a depth d. The vent chamber 48 may have a rectangular configuration with a length L and a width W. As shown, the length L of the vent chamber may extend in a direction along the microchannel 30 with the width W being transverse, such as perpendicular, to the length. The vent chamber 48 may have the same depth as the reaction chamber to facilitate venting of gas from the entire reaction chamber. The reaction chamber 46 may be fluidly coupled to the vent chamber by an entrance or stricture 50 defined by the width W of the vent chamber and the depth d of the chambers. In other embodiments, the depth of the vent chamber may be less than the reaction chamber, particularly should it be desired to entrap a defined amount of gas and form a bubble within the reaction chamber.

The capillary effect of the microchamber 28 may be affected by dimensional relationships associated with the chambers. For example, the capillary effect may be impacted by the diameter-to-width ratio D/W between the reaction chamber 46 and the vent chamber 48, the length-to-width ratio L/W of the vent chamber 48, and the depth-to-diameter ratio d/D of the reaction chamber 46.

In one illustrative embodiment, the microchamber 28 may be configured with a diameter-to-width ratio of D/W≥2 and a length-to-width ratio of L/W≥1. A microchamber configuration with these ratios is suitable for a microchamber configuration with a reaction chamber having a depth-to-diameter ratio of d/D≤2. For example, and without limitation, a depth-to-diameter ratio d/D of 1.5 may be employed with D/W≥2 and L/W≥1. However, it is to be appreciated that other ratios may be employed for the microchamber to achieve a desired level of surface tension or capillary effect. In other embodiments, the vent chamber 48 may have a length-to-width ratio of L/W≥0.7, a length-to-width ratio of L/W≥0.8, a length-to-width ratio of L/W≥0.9, or a length-to-width ratio of L/W≥1.

The capillary effect may also be affected by geometric aspects of the chambers. For example, and without limitation, the edge configuration of the entrance 50 to the vent chamber 48 may affect the amount of surface tension holding back the fluid from entering the vent chamber. More particularly, a relatively sharp edge may result in a higher surface tension as compared to a more rounded edge. In one embodiment, the microchamber may be configured with a relatively sharp edge at the entrance to the vent chamber to enhance surface tension and retain the fluid within the reaction chamber until the volume of fluid within the reaction chamber creates sufficient fluid pressure to overcome the surface tension. The microchamber may be configured so that this occurs when the reaction chamber is free of air bubbles.

Other dimensional relationships associated with features of the microchamber and/or microfluidic circuit may also affect the flow of the fluid sample and/or entrapment of bubbles within the microchamber. For example, fluid flow and/or bubble entrapment may be affected by the depth ratio between the reaction chamber 46 and the microfluidic channel 30, and the depth ratio between the reaction chamber 46 and the vent chamber 48. In one embodiment, the reaction chamber and the microfluidic channel may have a depth ratio of $d/d_2 \geq 2:1$. In one embodiment, the depth of the vent chamber may be at least 50% of the reaction chamber depth. However, it is to be appreciated that other depth ratios may be employed as should be apparent to one of skill in the art.

In one illustrative embodiment, the microchamber 28 may be configured with the reaction chamber 46 having a diameter D of 60 μm and the vent chamber 48 having a width W of 25 μm and a length L of about 16 μm. The reaction chamber and the vent chamber may each have a depth d of 100 μm. The microchamber may also have a total length $L_2$ extending in the direction of the microchannel 30 and across the diameter D of the reaction chamber to the end wall 52 of the vent chamber of 75 μm. Preferably, the reaction chamber diameter may be 30 μm to 600 μm. However, a reaction chamber with a diameter less than 30 μm may be used for some applications. Similarly, the reaction chamber may be configured with a diameter greater than 600 μm, although the surface tension effects may decrease and become less effective as the diameter increases above 600 μm.

Figure 2:
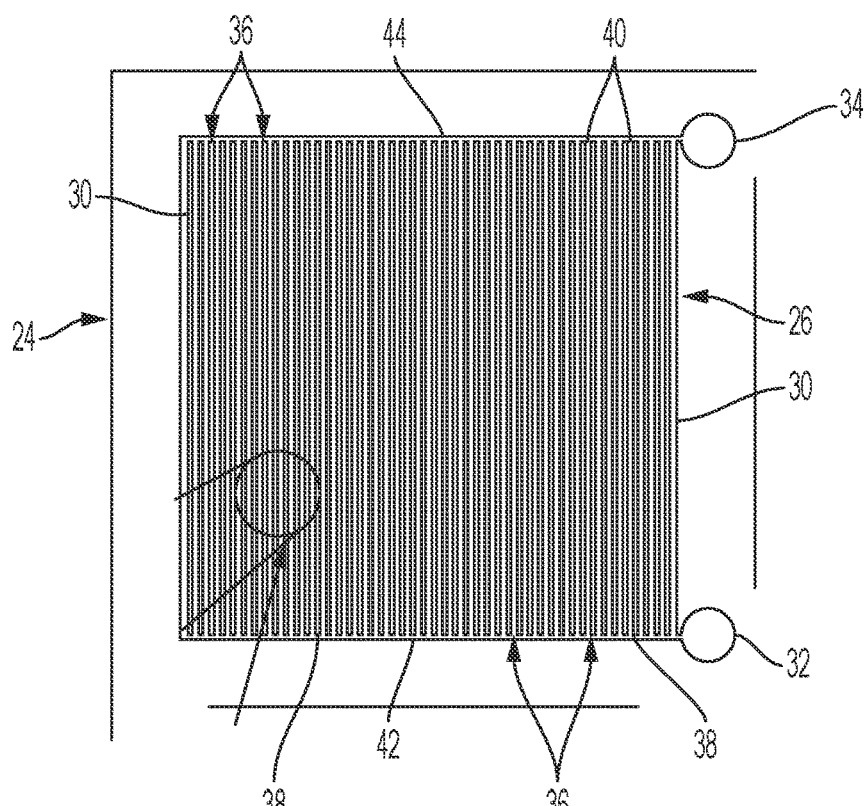
FIG. 2 is an enlarged view of a well of the microfluidic device of FIG. 1 illustrating a microfluidic circuit according to one embodiment.

In one illustrative embodiment, the microfluidic circuit of each well 24 may be arranged to include approximately one hundred-sixteen (116) groups of microchambers 28 with each group including approximately seventy-four (74) microchambers fluidly coupled together with a microfluidic channel 30 resulting in the well having more than eighty-five hundred (8500) microchambers for receiving separate portions of the fluid sample. As illustrated in FIGS. 2-3, the groups 36 of microchambers may be arranged in a linear pattern extending across the well. The microfluidic circuit may be arranged to direct the fluid sample to flow through each group in parallel to each other and with the microchambers in each group being arranged in series. However, it is to be appreciated that the microfluidic circuit may be employ any suitable configuration as should be apparent to one of skill in the art.

In one illustrative embodiment, each group of microchambers may arranged with a spacing $S_1$ of approximately 70 μm from an adjacent group. As shown in FIG. 3, the microchambers in adjacent groups may be arranged with an offset $S_2$ of approximately 55 μm to further increase the density of the microchambers within the well. Each microfluidic channel or connecting segment of a microfluidic channel may have a width $W_2$ of approximately 45 μm and a depth $d_2$ of approximately 20 μm. However, it is to be appreciated that the microfluidic circuit may employ any suitable spacing between microchambers and any suitable microfluidic channel sizes as should be apparent to one of skill in the art.

In one illustrative embodiment as shown in FIG. 1, the microfluidic device may include a microplate with ninety-six (96) wells arranged in a 8×12 grid arrangement. Each well may have a 9 mm×9 mm square configuration. The overall size of the microplate may be 72 mm×108 mm. Such an arrangement may provide in excess of 760,000 microchambers per microplate. It is to be understood that the microfluidic device may employ other suitable arrangements of wells as should be apparent to one of skill in the art.

The microfluidic device may be fabricated from any suitable material using any suitable manufacturing techniques as should be apparent to one of skill in the art.

In one illustrative embodiment, the microfluidic device may be formed from multiple layers of material. The layers of the microfluidic device may be composed of similar or different materials. In one embodiment, the microfluidic device may include a hydrophobic material to enhance the capillary effect within the microchamber for controlling the flow of fluid and air to the vent chamber as the reaction chamber is receiving fluid.

In some embodiments, a layer of the device may be made of a relatively rigid plastic, for example, polypropylene, polyethylene, polycarbonate, PTFE, and the like. Some plastics, such as PTFE, polypropylene, are naturally hydrophobic, so they may improve the performance of the capillary effect preventing liquid from prematurely flowing into the vent chamber. Alternatively, a layer may include a flexible, rubber-like material such as silicone or other elastomer. Other potential materials may include glass, ceramics, silicon, or the like. As such, a layer may be rigid or deformable. Such materials may be translucent or clear so as to easily allow for optical measurements of the contents within the chambers/cavities.

Individual layers of the microfluidic device may be made by any suitable method. In some embodiments, layers are fabricated via injection molding, by embossing the cavities and channels into a thin sheet of plastic, etching, or any other suitable method. For example, spaces that define the cavities and channels may be formed (e.g., molded, etched) in a plastic/polymer or elastomeric material that makes up the layer.

In some embodiments, different layers may define cavities and channels that are initially in fluid communication. For example, a first layer may define a number of cavities without defining the channels that connect the cavities together; an additional layer adjacent to the first layer may define those channels that connect the cavities. Such channels may be appropriately sealed, for example, by compression of the two layers relative to each other.

In some embodiments, a layer may include acrylic adhesive, natural rubber adhesive, or silicone adhesive. Such materials may be suitable to deform into channels of the device (e.g., as a sealing material) when subject to compression. In some embodiments, adhesives may be disposed on a relatively rigid layer, or alternatively, on a separate backing. Examples of suitable backings may include, but are not limited to, polypropylene, polyethylene, polycarbonate, and/or other suitable plastics.

Various components (e.g., layers, adhesives, etc.) of a microfluidic device may be adhered together by any suitable method. For example, an adhesive may be used to bond one or more components together, such as for bonding a separating/sealing material and first and/or second layers. In some embodiments, the components of the microfluidic device may be compressed together (e.g., via clamping, rolling, or other externally applied force) so as to result in an evenly distributed bond between surfaces of different layers.

For certain materials, the application of an appropriate amount of compression and/or heat may result in changes to certain characteristics of the components of the device. For example, at elevated temperatures, certain materials such as wax will become increasingly tacky and/or adhesive, resulting in strong adherence between components of the device. Accordingly, the different layers of the device, including a wax layer, may be assembled and then subject to compression and heating for an appropriate period of time, allowing the wax to create a bond. In some embodiments, one or more appropriate solvents may be used to promote bonding between layers.

FIGS. 6-11 illustrate one example of the flow of fluid and air into and from a microchamber as a fluid sample flows through the microfluidic circuit of a well.

Figure 6:
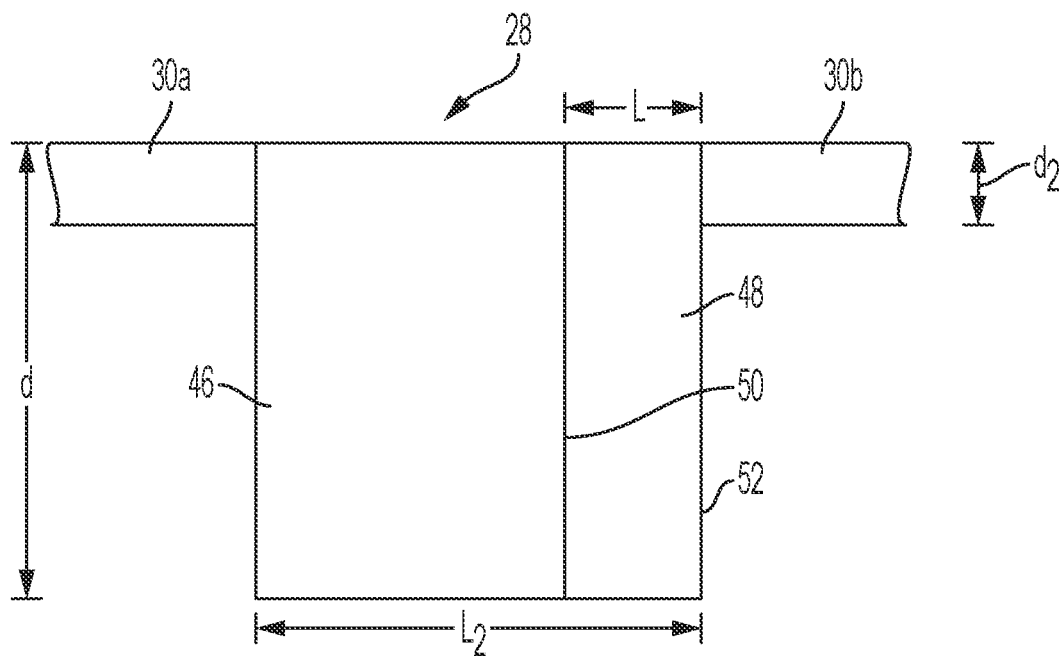
FIG. 6 is a cross-sectional view of the microchamber circuit taken along section line 6-6 of FIG. 5.

FIG. 6 illustrates a microchamber 28 containing only air, or some other gas, prior to the introduction of a fluid sample.

Figure 7:
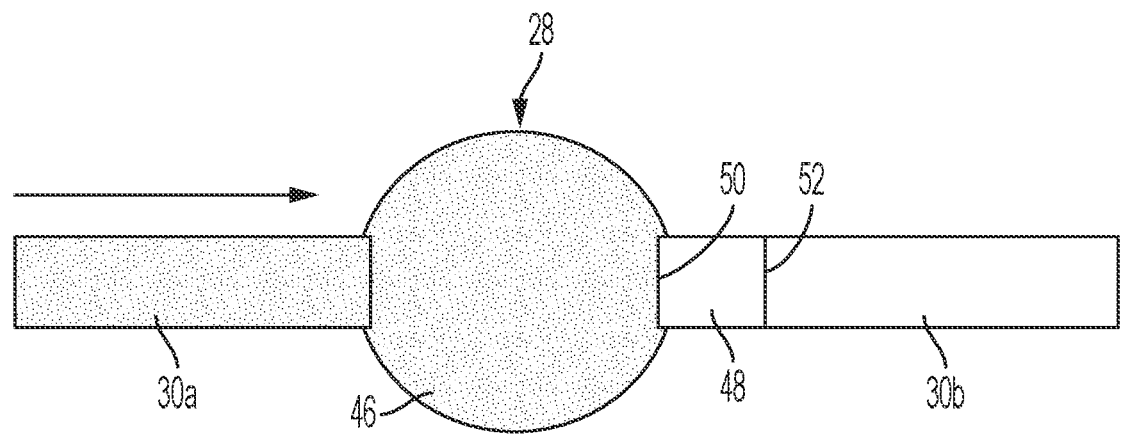
FIG. 7 is a top view of the microchamber of FIGS. 5-6 receiving a fluid sample therein.
Figure 8:
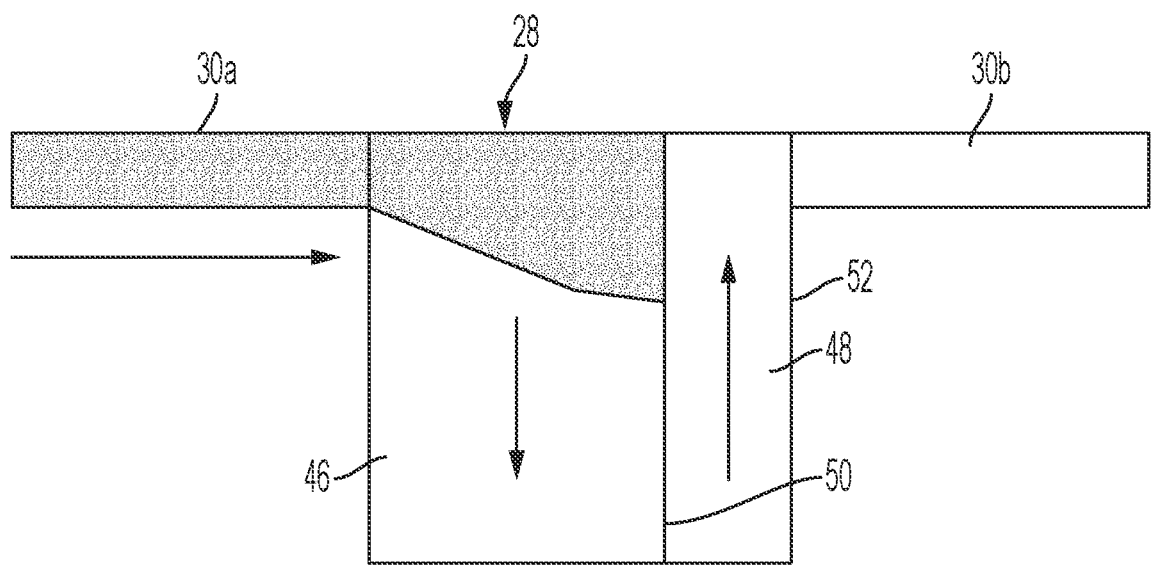
FIG. 8 a schematic illustration of FIG. 6 with the fluid sample partially filling a reaction chamber and air being vented through a vent chamber.

FIGS. 7-8 illustrate the fluid sample entering the reaction chamber 46 and displacing air into the vent chamber 48. Although FIG. 8 illustrates the fluid sample flowing in a downward direction as it enters the reaction chamber, the microfluidic device would typically be oriented so that the fluid sample actually enters the bottom of the reaction chamber and flows in an upward direction. In this regard, FIGS. 6-11 illustrate the microchamber rotated 180° from how it would typically be oriented in use with the microfluidic device.

Figure 9:
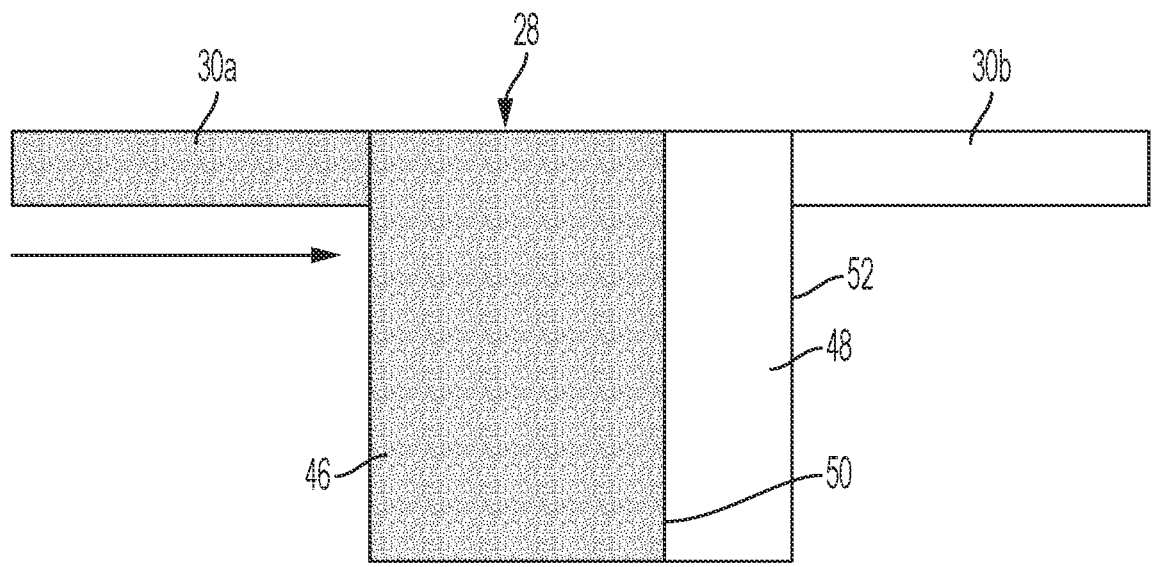
FIG. 9 is a schematic illustration of FIG. 6 with the fluid sample filling the reaction chamber and being held in the reaction chamber by the stricture to the vent chamber.

FIG. 9 illustrates the reaction chamber 46 filled with the fluid sample and free of air bubbles due to the venting of air from the reaction chamber. As illustrated, the fluid is maintained in the reaction chamber 46 by the surface tension created at the entrance 50 to the vent chamber 48.

Figure 10:
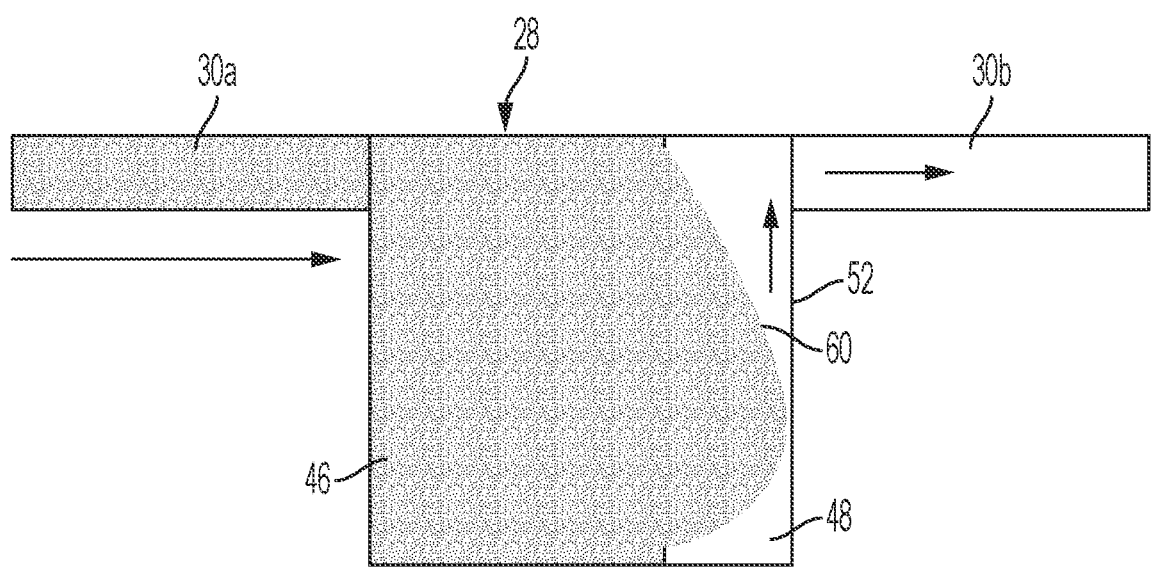
FIG. 10 is a schematic illustration of FIG. 6 with fluid pressure increasing in the reaction chamber causing the free surface to protrude beyond the stricture and into the vent chamber prior to the fluid overcoming surface tension holding the fluid in the reaction chamber.
Figure 11:
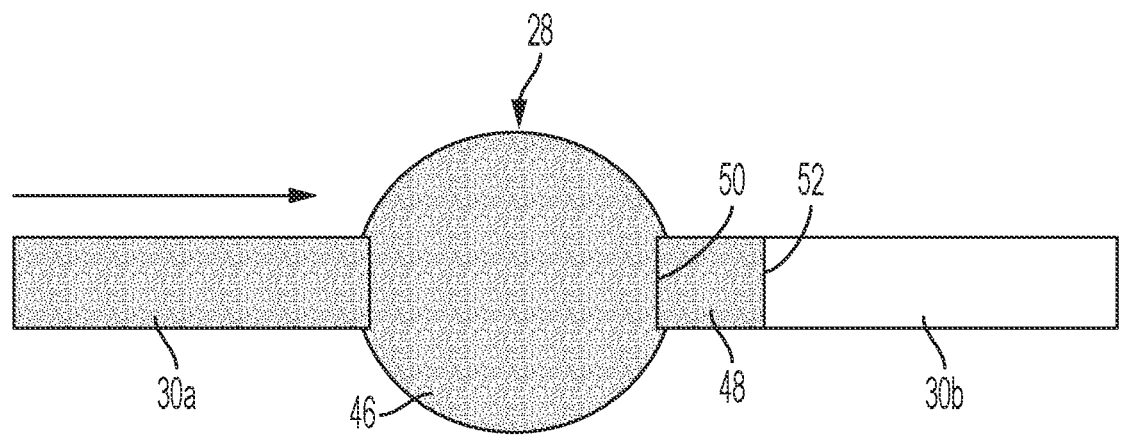
FIG. 11 is a top schematic view of the microchamber of FIG. 10.

As illustrated in FIGS. 10-11, an increase in the fluid pressure within the reaction chamber 46 causes the free surface 60 of the fluid to protrude through the entrance 50 until the fluid pressure overcomes the surface tension and the fluid flows into the vent chamber 48. As illustrated in FIG. 10, it may be possible for an air bubble to become trapped within the vent chamber 48 depending on where and how quickly the fluid breaks through the stricture. However, an air bubble trapped within a portion of the vent chamber would not be expected to adversely impact the reaction occurring within the reaction chamber.

FIGS. 12-19 illustrate an example of a fluid sample being introduced through a microfluidic circuit of a well of a microfluidic device for undergoing a dPCR or other technique related to molecular biology.

Figure 12:
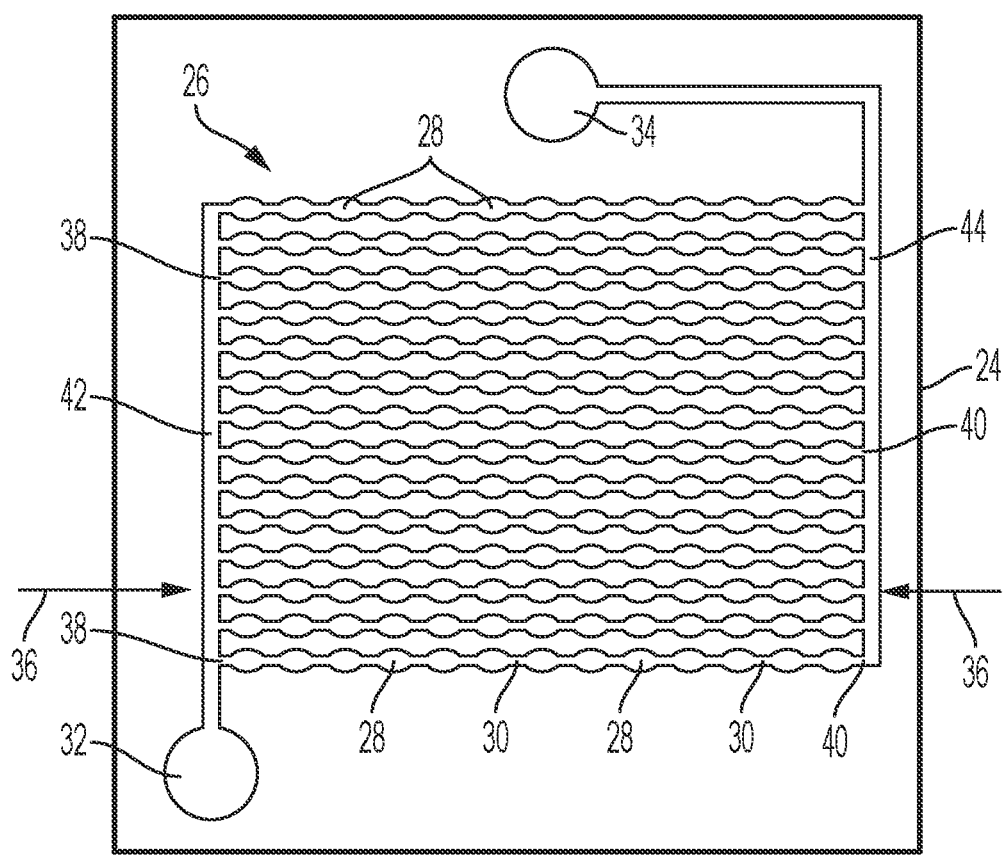
FIG. 12 is a schematic view of a microplate well illustrating a representative fluid circuit of microchambers.

FIG. 12 is a schematic illustration of a microplate well 22 with a microfluidic circuit 26 prior to introduction of a fluid sample. The microfluidic circuit includes fourteen (14) groups 26 of microchambers 28 arranged in parallel and each group including thirteen (13) microchambers fluidly coupled in series by a microfluidic channel. A first end 38 of each microfluidic channel 30 is fluidly coupled to an inlet channel 42 and a second end 40 of each microfluidic channel 30 is fluidly coupled to an outlet channel 44. A circuit inlet 32 is coupled to the inlet channel 42 and a circuit vent 34 is coupled to the outlet channel 44.

Figure 13:
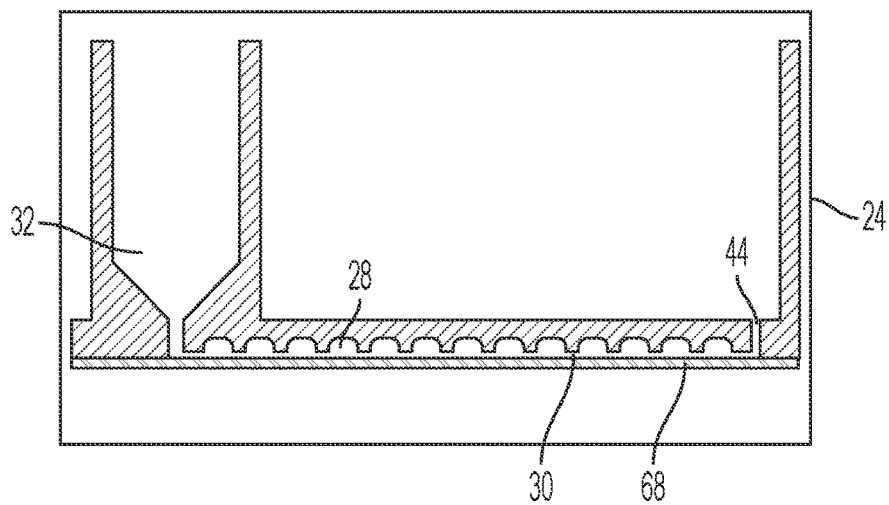
FIG. 13 is a cross-sectional view of the microplate taken along section line 13-13 of FIG. 13 illustrating a group of fluidly coupled microchambers.

FIG. 13 is a side view of the well of FIG. 12 illustrating the circuit inlet and a group of the microchambers fluidly coupled by a microfluidic channel.

Figure 14A:
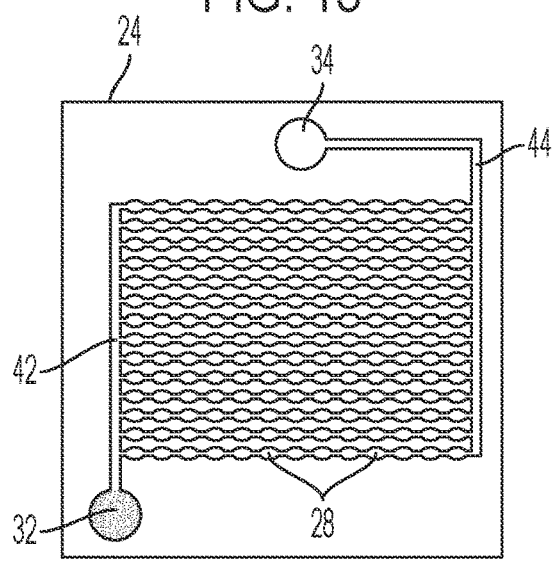
FIG. 14A-B depicts a schematic illustration of a well 24 with a circuit inlet 32 is coupled to the inlet channel 42 in fluid communication with a plurality of microchambers 28 arranged in parallel coupled to an outlet channel 44 coupled to a circuit vent 34 [top view (A)]. A well 24 comprises a plurality of microchambers 28 arranged in series 30 coupled to a circuit inlet 32 configured to receive a fluid sample that is to be distributed throughout the microfluidic circuit coupled to an outlet channel 44. A bottom seal 68 of the microplate blocks off the microfluidic 30 channels and isolated the fluid samples held by each of the microchambers 28 [side view (B)].
Figure 14B:
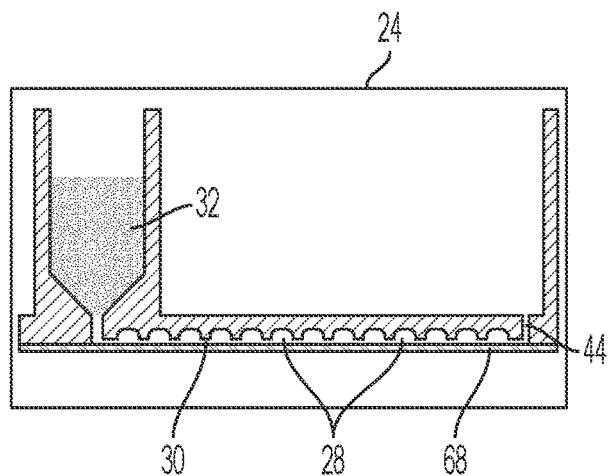

As illustrated in FIGS. 14A-14B, a fluid sample, such as a PCR reaction mixture, is delivered to the circuit inlet 32.

In one embodiment, a pipette may be used to deliver the PCR reaction mixture to the inlet.

Figure 15:
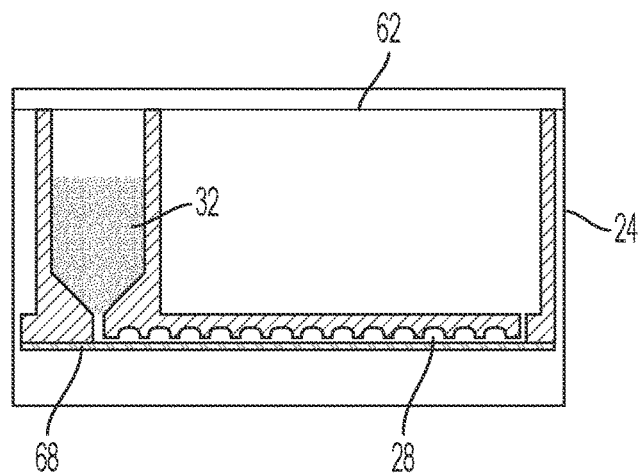
FIG. 15 (side view) depicts a flexible plate seal 62 is applied to the top of the microplate and over each well 24 comprising a plurality of microchambers 28 with the PCR reaction mixture remaining in the circuit inlet 32. A bottom seal 68 of the microplate blocks off the microfluidic 30 channels and isolated the fluid samples held by each of the microchambers 28. The microplate is thereafter placed into an instrument for conducting a dPCR technique on the mixture.

As illustrated in FIG. 15, a flexible plate seal 62 is applied to the top of the microplate 22 and over each well 24 with the PCR reaction mixture remaining in the circuit inlet 32. The microplate is thereafter placed into an instrument for conducting a dPCR technique on the mixture. For example, and without limitation, the microplate may be particularly suited for use with the CONSTELLATION Digital PCR System available from Formulatrix of Bedford, Mass.

Figure 16A:
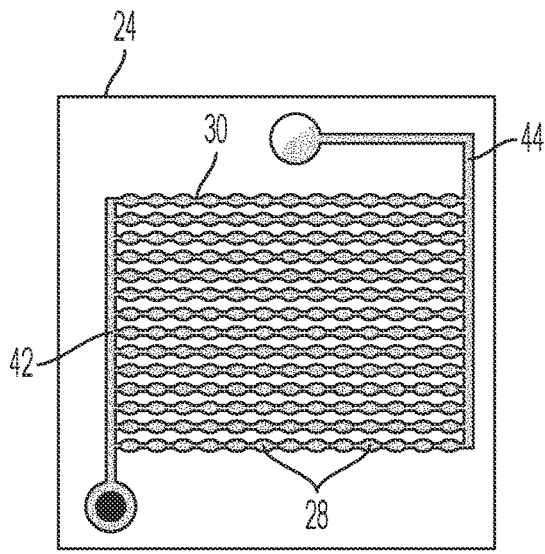
FIG. 16A-B depicts a schematic illustration of a well 24 with an inlet channel 42 in fluid communication with a plurality of microchambers 28 coupled to an outlet channel 44 coupled to a circuit vent 34 [top view (A)].
Figure 16B:
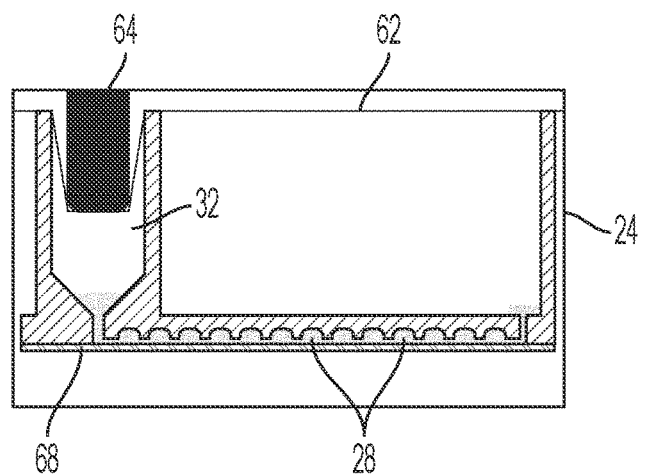

Once placed in the instrument, the fluid sample is loaded into each microchamber 28 by moving the fluid through the microfluidic circuit 26 and venting air within the circuit from the circuit vent 34. As illustrated in FIGS. 16A-16B, the fluid sample may be injected into the microfluidic circuit 26 using a piston 64 or other suitable device which presses the plate seal 62 into the circuit inlet 32 to create a pressure differential between the circuit inlet and circuit vent causing the fluid to flow through the microfluidic circuit. In addition to air, excess fluid within the microfluidic circuit may exit through the circuit vent 34.

With the microfluidic circuit filled with the fluid sample, a roller 66 may be used to compress a bottom seal 68 of the microplate, as illustrated in FIGS. 17A-17B, to block off the microfluidic channels 30 and isolate the fluid samples held by each of the microchambers 28, as illustrated in FIGS. 18A-18B. Thereafter, the microplate may be thermocycled by the instrument to expose the reactants within each microchamber to cycles of repeated heating and cooling, thereby permitting different temperature-dependent reactions. For example, and without limitation, thermocycling the microplate may result in a doubling of a target DNA with each cycle.

Figure 19A:
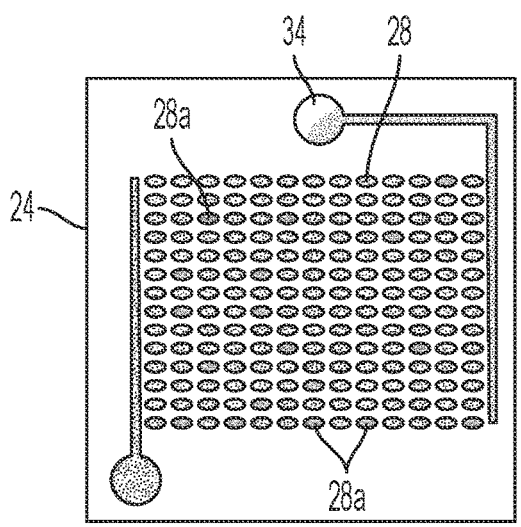
Figure 19B:
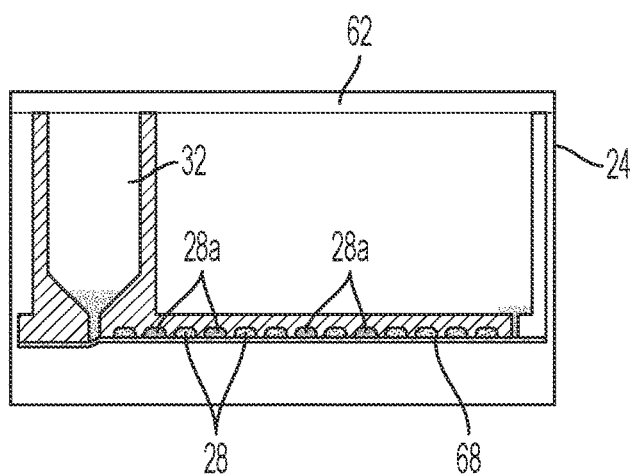

As illustrated in FIGS. 19A-19B, the microchambers 28a containing the target DNA become fluorescent. The microplate may then be imaged by the instrument to count the number of positive microchambers.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

The foregoing description of various embodiments are intended merely to be illustrative thereof and that other embodiments, modifications, and equivalents are within the scope of the claims appended hereto.

What is claimed is:

1. A microfluidic device for handling a fluid sample, the microfluidic device comprising:
   at least one microfluidic well configured to receive the fluid sample; and
   a microfluidic circuit provided in the at least one microfluidic well, the microfluidic circuit configured to distribute the fluid sample within the at least one microfluidic well;
   the microfluidic circuit including a plurality of reaction chambers, at least one microfluidic channel fluidly coupling the plurality of reaction chambers, and a plurality of microfluidic valves associated with the plurality of reaction chambers, each microfluidic valve being fluidly coupled to an associated reaction chamber;
   each reaction chamber configured to receive a fluid sample from the at least one microfluidic channel and each microfluidic valve configured to vent gas from a corresponding reaction chamber via the at least one microfluidic channel as the fluid sample flows into the reaction chamber,
   wherein each reaction chamber is arranged in the microfluidic circuit to receive fluid from an upstream segment of the at least one microfluidic channel and each microfluidic valve is arranged in the microfluidic circuit to deliver fluid to a downstream segment of the at least one microfluidic channel.

2. The microfluidic device according to claim 1, wherein the plurality of reaction chambers includes first and second reaction chambers, one of the plurality of microfluidic valves being located between the first and second reaction chambers.

3. The microfluidic device according to claim 2, wherein the first reaction chamber is fluidly coupled to the microfluidic valve and the microfluidic valve is fluidly coupled to the second reaction chamber, the microfluidic circuit being arranged to direct the fluid sample to flow from the first reaction chamber through the microfluidic valve to the second reaction chamber.

4. The microfluidic device according to claim 3, wherein the microfluidic valve is configured to restrict the flow of the fluid sample from the first reaction chamber until the first reaction chamber is essentially free of air.

5. The microfluidic device according to claim 1, wherein each microfluidic valve is configured to be a passive valve.

6. The microfluidic device according to claim 1, wherein each microfluidic valve is formed of a hydrophobic material.

7. The microfluidic device according to claim 6, wherein each microfluidic valve is formed from one or more of polypropylene, polyethylene and PTFE.

8. A method of handling a fluid sample, the method comprising acts of:
   (a) delivering a fluid sample to a microfluidic device including a plurality of microchambers and at least one microfluidic channel fluidly coupling the plurality of microchambers, each microchamber including a reaction chamber and a vent chamber fluidly coupled to the reaction chamber;
   (b) directing the fluid sample into the reaction chamber of each microchamber through a first segment of the at least one microfluidic channel; and
   (c) venting gas from the reaction chamber via the vent chamber through a second segment of the at least one microfluidic channel as the fluid sample flows into the reaction chamber, directing the fluid sample to flow from the reaction chamber to the vent chamber, and directing the fluid sample to flow from the vent chamber to the second segment of the at least one microfluidic channel.

9. The method according to claim 8, wherein during act (c), the fluid sample is released from the reaction chamber into the vent chamber when the gas has been vented from the reaction chamber and the reaction chamber is essentially free of air.

10. The method according to claim 8, wherein the plurality of microchambers includes first, second and third microchambers fluidly coupled by the at least one microfluidic channel, the first segment of the at least one microfluidic channel fluidly coupling the first and second microchambers and the second segment of the at least one microfluidic channel fluidly coupling the second and third microchambers.

11. The method according to claim 8, further comprising act (d) of performing digital PCR in the microfluidic device after filling the reaction chambers with the fluid sample.

* * * * *